United States Patent [19]

Nappa et al.

[11] Patent Number: 5,866,728
[45] Date of Patent: Feb. 2, 1999

[54] USE OF ALKALI METAL HALIDES IN THE MANUFACTURE OF 1, 1-DIFLUOROETHANE

[75] Inventors: Mario Joseph Nappa, Newark; William Robert Williams, Wilmington, both of Del.

[73] Assignee: E. I. Dupont De Nemours and Company, Wilmington, Del.

[21] Appl. No.: 583,331

[22] Filed: Jan. 5, 1996

[51] Int. Cl.[6] ................................................. C07C 17/08
[52] U.S. Cl. ........................................................ 570/166
[58] Field of Search ............................................. 570/166

[56] References Cited

U.S. PATENT DOCUMENTS

| | | | |
|---|---|---|---|
| 2,830,099 | 4/1958 | Swamer | 260/653 |
| 3,317,619 | 5/1967 | Hedge et al. | 260/653.3 |
| 3,536,769 | 10/1970 | Seki et al. | 260/653.6 |
| 3,904,701 | 9/1975 | Schultz et al. | 570/166 |
| 4,147,733 | 4/1979 | Fiske et al. | 260/653.4 |
| 4,766,258 | 8/1988 | Komatsu et al. | 570/168 |
| 4,968,850 | 11/1990 | Franklin et al. | 570/166 |
| 5,208,395 | 5/1993 | Elsheikh | 570/166 |
| 5,306,850 | 4/1994 | Darago | 570/178 |
| 5,396,001 | 3/1995 | Pennetreau | 870/179 |

FOREIGN PATENT DOCUMENTS

| | | |
|---|---|---|
| 0 187 643 | 7/1986 | European Pat. Off. . |
| 637 579 A1 | 8/1995 | European Pat. Off. . |
| 676386-A1 | 10/1995 | European Pat. Off. . |
| 246528 | 10/1987 | Japan . |
| 8-5816 | 1/1996 | Japan . |
| 341788 | 6/1972 | Russian Federation . |
| 341788 | 12/1972 | Russian Federation . |
| 466202 | 4/1975 | Russian Federation . |

OTHER PUBLICATIONS

A. F. Clifford, et al. The Hydrogen Fluoride Solvent System—I. A Qualitative Survey of Acids. J. Inorg. Chem. 1957, vol. 5 pp. 57 to 70.

L. E. Levchuk, et al. Synthesis and Mössbauer and Vibrational Spectra of Some New Tin(IV)—Flourine Compounds. Inorganic Chemistry, vol. 11, No. 1, 1972, pp. 43 to 50.

*Primary Examiner*—Alan Siegel

[57] ABSTRACT

A process is disclosed for the selective and high yield preparation of 1,1-difluoroethane (HFC-152a). The process comprises contacting chloroethene with anhydrous hydrogen fluoride in a liquid phase at a temperature from about 50° C. and 95° C. while in the presence of a tin(IV) catalyst and an alkali metal halide.

17 Claims, 1 Drawing Sheet

FIG.1

USE OF ALKALI METAL HALIDES IN THE MANUFACTURE OF 1, 1-DIFLUOROETHANE

BACKGROUND OF THE INVENTION

Golubev et al. (U.S.S.R. Inventor Certificate No. 341,788, published Jul. 7, 1972) describe a liquid phase process for producing 1,1-difluoroethane (HFC-152a) by reacting chloroethene with hydrogen fluoride (HF) while in the presence of tin tetrachloride ($SnCl_4$).

Komatsu et al. (European Patent EP 187,643, filed Jan. 3, 1986) discloses a process for manufacturing hydrofluorocarbons by reacting hydrochlorocarbons with HF while in the presence of a tin catalyst and an additive chosen from compounds containing oxygen or nitrogen. These additives, however, have low stability in the reaction medium and/or reduce the activity of the tin catalyst when used in the presence of HF and a hydrochlorocarbon such as 1,1,2-trichloroethane.

U.S. Pat. No. 4,968,850 to Franklin et al., discloses a process for manufacturing a fluorinated hydrocarbon by reacting hydrogen fluoride with an unsaturated chlorinated hydrocarbon while in the presence of a tin catalyst.

Komatsu et al. (Japanese Kokai publication number SHO 62[1987]-246528, publication date Oct. 27, 1987) describes a process for manufacturing hydrofluorocarbons, characterized by reacting a hydrogen-containing halogenated hydrocarbon with HF in a liquid phase.

The disclosure of the above-identified patent documents is hereby incorporated by reference.

FIELD OF THE INVENTION

The present invention relates to a process for the selective and high yield preparation of 1,1-difluoroethane by contacting chloroethene with hydrogen fluoride in a liquid phase while in the presence of a tin catalyst and an additive comprising at least one alkali metal halide.

CROSS-REFERENCE TO RELATED PATENTS AND PATENT APPLICATIONS

The subject matter of this invention is related to the following copending and commonly assigned U.S. patent applications: (1) Provisional U.S. patent application No. 06/009,871, filed on even date herewith in the names of Mario J. Nappa et al., and entitled "Process For Producing 1,1-Difluoroethane"; and (2) Provisional U.S. patent application No. 06/009,668, filed on even date herewith in the names of Mario J. Nappa et al., and entitled "Process For Preparation Of Fluorinated Hydrocarbons".

The subject matter of this invention is also related to the following copending and commonly assigned U.S. patent applications: (1) U.S. patent application Ser. No. 08/468,099 (Attorney's Docket No. CH-2511), filed on Jun. 6, 1995 in the name of Maria U. D. Beug-Deeb et al., and entitled "Azeotropic Or Azeotrope-Like Compositions Of Hydrofluoric Acid With Dihaloethanes"; (2) U.S. patent application Ser. No. 08/474,884 (Attorney's Docket No. CH-2512), filed on Jun. 7, 1995 in the name of Klaus Guenter Wuttke, and entitled "Continuous Manufacture Of 1,1-Difluoroethane"; (3) U.S. patent application Ser. No. 08/476,770 (Attorney's Docket No. CH-2529), filed on Jun. 7, 1995 in the name of Mario Joseph Nappa et al., and entitled "Two-Step Process For Manufacturing 1,1-Difluoroethane"; and, (4) U.S. patent application Ser. No. 08/480,066 (Attorney's Docket No. CH-2530), filed on Jun. 7, 1995 in the name of Wendel Richard Cassel et al., and entitled "Manufacture Of 1,1-Difluoroethane By Reactive Distillation".

The disclosure of the above-identified copending and commonly assigned U.S. Patent Applications is hereby incorporated by reference.

SUMMARY OF THE INVENTION

This invention is a process for making HFC-152a (1,1-difluoroethane, $CH_3CHF_2$) from chloroethene while minimizing formation of oligomeric and polymeric byproducts such as 1,3-dichloro-1-fluorobutane and homologous higher alkanes, among others. These byproducts are also conventionally known as "tars". The term "tar" refers to compounds of fairly low molecular weight formed as a result of dimerization or trimerization of the halogenated carbon compounds and their fluorinated adducts. The term "tar" further refers to higher molecular weight, e.g., predominately 50,000, with standard weight fraction distribution from 2,000 to 75,000, number averaged molecular weight branched, polymeric, halogenated hydrocarbons, which may contain metal species acquired from catalyst and other additives, if present. Such higher molecular weight materials can be formed by polymerization of lower molecular weight dimers, trimers, and oligomers with themselves or with the halogenated carbon compounds and their fluorinated adducts. The inventive process can minimize tar formation while selectively producing HFC-152a.

Conventional processes for making HFC-152a are undesirable due to the high amounts of byproducts/tars produced. The inventive process solves the problems associated with conventional processes by reducing the tar formation rates.

The invention can be practiced by providing HF, one or more additives and one or more catalyst in any desirable sequence or combination. After providing the aforementioned components, such are contacted with chloroethene. One aspect of the invention comprises (1) providing a liquid phase comprising chloroethene, HF, a tin catalyst, and at least one additive selected from the family of alkali metal halides, (2) heating the mixture and (3) recovering HFC-152a. The liquid phase components may be introduced into a reaction vessel in any order; but typically, the vessel is charged with a tin catalyst and an alkali metal halide followed by HF, e.g., anhydrous HF, and chloroethene. The temperature of the resultant mixture within the vessel is then adjusted to about 20° to about 130° C., normally 50° to 95° C.

If desired, chloroethene can be added continuously or batchwise to the reaction vessel whereupon HFC-152a can be distilled out of the liquid phase and removed from the reaction vessel. If desired, HF, a tin catalyst and an alkali metal halide can be added to the reaction vessel in a continuous fashion along with chloroethene. By analyzing products formed by this process, it was determined that the inventive process achieves high yields and selective conversion of chloroethene to HFC-152a while minimizing formation of oligomeric and polymeric byproducts, e.g., tars.

BRIEF DESCRIPTION OF THE DRAWING

FIG. 1 is a schematic diagram of a continuous process used to produce HFC-152a.

DETAILED DESCRIPTION

Processes for preparing hydrofluorocarbons (HFCs) and hydrochlorofluorocarbons (HCFCs) from hydrochlorocarbons (HCCs) and anhydrous hydrogen fluoride (HF) by metal mediated halogen exchange have found wide industrial utility. The industrial process is one in which carbon to chlorine bonds of the hydrochlorocarbon are broken and replaced with carbon to fluorine bonds. A metal species acts in a catalytic capacity. HFC-152a has been manufactured in this manner by using liquid or gas phase processes. HFC-152a has been prepared by allowing chloroethene to react with HF while in the presence of salts of various oxidized metals, wherein metal species such as tin(IV), titanium(IV), antimony(III), and antimony(V) are employed. Intermediates and by-products from the conventional procedures comprise at least one of 1-chloro-1-fluoroethane (HCFC-151a), 1,1-dichloroethane (HCC-150a), an assortment of oligomeric and polymeric materials, low molecular weight halogenated dimers and oligomers through higher molecular weight halogenated polymers taking the form of oils, tars, e.g., having a molecular weight greater than about 1500 gm/mole, dark carbonaceous solids, among other byproducts. These byproducts are detrimental to the exchange process because such can interfere with catalyst activity, reduce reactor volume, decrease the yield of HFC-152a, become a disposal concern, among other detrimental aspects.

HFC-152a is a compound having a wide range of industrial utility. HFC-152a can be employed either alone or in blends with other materials as an aerosol, a refrigerant, blowing agent, propellant, cleaning agent, as an intermediate for making other fluorocarbon compounds such as fluoroethene, among other uses.

The inventive process comprises selectively preparing HFC-152a from chloroethene while minimizing the formation of oligomeric and polymeric byproducts. The process comprises providing chloroethene, HF, a tin catalyst, one or more members from the family of alkali metal halides, and heating the resultant mixture and recovering HFC-152a. The recovered HFC-152a can be substantially pure, e.g., 90 to about 100% wt % pure HFC-152a. If desired, chloroethene can be mixed with one or more compounds such as HCC-150a as well as compounds typically present in commercially available chloroethene. While any suitable tin catalysts, e.g., $SnX_4$ wherein X comprises one or more halides, can be employed specific examples of such catalyst comprise or consist essentially of at least one of tin halides, tin oxyhalides, organotins, among others. A specific example of a desirable tin halide comprises or consists essentially of tin(IV) chloride ($SnCl_4$). Other examples of tin(IV) halides include one or more of $SnBr_4$, $SnCl_3F$, $SnCl_2F_2$, $SnClF_3$, $SnF_4$, among others. The tin chlorofluorides can be generated, e.g., formed in situ, when $SnCl_4$ contacts HF. Specific examples of suitable tin oxyhalide compounds comprise or consist essentially of at least one member selected from the group of $SnCl_2O$, $SnF_2O$, and $SnClFO$. Suitable organotin catalysts include compounds in which a tin atom is bonded to from one to four carbon atoms, e.g., tetramethyl tin ($Sn(CH_3)_4$), oxydiethyl tin ($OSn(C_2H_5)_2$), dichlorodimethyl tin ($SnCl_2(CH_3)_2$), among others.

The alkali metal halide have a general empirical formula of MX; wherein M is at least one Group IA alkali metal (Group IA from the periodic table of Lang's Handbook of Chemistry, fourteenth edition, John A. Dean Ed., McGraw Hill, Inc., 1992) such as lithium, sodium, potassium, rubidium, or cesium, and X is a group VIIA halogen such as fluorine, chlorine, bromine, or iodine.

The quantity of alkali metal halide or alkali metal halides employed in the inventive process is generally between about 0.001 mole and about 2 moles per mole of tin catalyst. Typically, the process is practiced by using between about 0.1 mole and about 1.5 moles alkali metal halide or alkali metal halides per mole of tin catalyst. NaCl is a particularly useful alkali metal halide.

In one aspect of the invention, one or more of the aforementioned alkali metal halides and catalysts can be combined prior to being contacted with chloroethene. For example, NaCl and $SnCl_4$ are premixed, e.g., a suspension $NaCl/SnCl_4$. The premixed halide/catalyst combination can be employed in any suitable batch or continuous process described herein.

In another aspect of the invention, employing from about 0.001 to about 5 moles of saturated halogenated hydrocarbon as additive per mole of tin catalyst, or such saturated halogenated hydrocarbon together with from about 0 to 2 moles of alkali metal halide per mole of tin catalyst, also leads to increased product selectivity and yields, and decreased formation of undesirable byproducts. The saturated halogenated hydrocarbons may be charged as pure compounds or in any composition of mixture to the process. Examples of saturated halogenated hydrocarbons are those which lead to increased product selectivity and yields, and decreased formation of undesirable byproducts. Such saturated hydrocarbons are comprised of members of $CX1X2X3X4$; wherein at least one of X1 through X4 is chlorine or contains chlorine and wherein the remaining X1 through X4 groups are independently or together comprised of H, F, Cl, Br, or $C(y)Z(2y+1)$, wherein Z is independently or together comprised of H, F, Cl, or Br, and y is an integer from 1 to 5. Examples of saturated halogenated hydrocarbon additives comprise at least one member selected from the group of methylene chloride, 1,2-dichloroethane, 1,1-dichloroethane, 1,1,1-trichloroethane, 1-chloro-1-fluoroethane, 2,2-dichloro-1,1,1-trifluoroethane, among others. Especially useful is 2,2-dichloro-1,1,1-trifluoroethane.

The Table following this paragraph list the results, which were achieved in the Examples, by operating one aspect of the inventive process. Table 1 illustrates the benefits of employing an alkali metal halide in the tin(IV) mediated synthesis of HFC-152a from chloroethene and HF. Without wishing to be bound by any theory or explanation, it is believed that when holding all other process variables constant and increasing the mole ratio of alkali metal halide to tin catalyst from 0 to about 1, adding an alkali metal halide causes a corresponding increase in the HFC-152a/HCFC-151a mole ratio. An increase in the mole ratio of alkali metal halide to tin catalyst may be accompanied by an increase in the molar yield of HFC-152a, and a decrease in the mass percent of tar formation. It is further believed that when the mole ratio of alkali metal halide additive to tin catalyst employed in the process is greater than 1, the process can be inhibited thereby causing a decrease in the HFC-152a/HCFC-151 a product ratio and an increase in tar formation. If the inventive process is operated at a mole ratio of alkali metal halide to tin catalyst of at least about 2, then the process performance can become relatively less effective in comparison to a process operating without an alkali metal halide. Thus, the window for most effectively operating the inventive process is relatively broad. That is, while any suitable amount of catalyst can be employed, a beneficial effect was normally observed when employing any mole ratio of alkali metal halide to tin catalyst between and including greater than about 0 to at least about 1.5; typically about 0.7 to about 1.3.

TABLE 1

Effect of Alkali Metal Halide to Tin Catalyst Mole Ratio on Product Distribution and Tar Formation

| Alkali Metal Halide | Mole Ratio of Alkali Metal Halide/ Tin Catalyst | Product Mole Ratio HFC-152a/ HCFC-151a | Molar Yield HFC-152a | Mass % Tars | Example Number |
|---|---|---|---|---|---|
| None | 0 | 41 | 85 | 2.3 | C1* |
| None | 0 | 44 | 87 | 2.0 | C2** |
| KF | 0.15 | 48 | 100 | 1.0 | 1 |
| KF | 0.30 | 58 | 100 | 0.7 | 2 |
| KF | 0.60 | 68 | 100 | 0.4 | 3 |
| KF | 1.00 | 78 | 88 | 0.2 | 5 |
| KCl | 1.00 | 96 | 87 | 0.1 | 6 |
| NaCl | 1.00 | 105 | 85 | 0.2 | 7 |
| NaF | 1.00 | 99 | 88 | 0.3 | 8 |
| KF | 1.90 | 21 | 96 | 4.9 | 4 |

*C1 = Comparative Example 1
**C2 = Comparative Example 2

Table 1 shows that using an alkali metal halide in a reaction mixture in which chloroethene is contacted with HF, in a liquid phase while in the presence of a tin catalyst, leads to increased selectivity to form HFC-152a and a reduction in the amount of tar. Table 1 also shows that certain tin catalysts such as tin(IV) halides, when modified by the instant additives, become more soluble in HF. Without wishing to be bound by any theory or explanation, it is believed that the increased solubility causes a decrease in polymerization. This effect is observed when comparing present Comparative Example 2 and Example 7.

In one aspect of the invention, the process is performed in a batch operation. Any suitable autoclave, such as a 450 cc Parr® Series 4560 Mini Reactor constructed of Hastelloy C®, is provided. The autoclave is typically fitted with a turbine impeller for agitating the liquid contents of the autoclave, a septum port for introducing or withdrawing liquids from the autoclave by syringe or cannula technique, valved ports for introducing or withdrawing gaseous or liquid materials, a jacketed 0.25 inch tube reflux condenser topped with a valved takeoff port, and an external heating jacket. The inventive batch method may generally be carried out on any scale desired. The equipment and associated feed lines, effluent lines, and associated units should be constructed of materials resistant to HF and HCl. Typical materials of construction, well-known to the fluorination art, include stainless steels and high nickel alloys, such as Monel® nickel-copper alloys, Hastelloy® nickel-based alloys, and Inconel® nickel-chromium alloys.

A dry autoclave is transferred into a dry-box and the desired amount of at least one tin catalyst and at least one alkali metal halide are charged to the autoclave. The tin catalysts are normally loaded into the autoclave while within a dry-box in order to minimize any reaction between the tin compounds and moisture present in the air.

The autoclave is sealed, and removed from the drybox. A port of the autoclave is then attached to a vacuum pump and the lower portion cooled by being placed into liquid nitrogen, and the vessel is evacuated. By establishing a vacuum in the autoclave system, potentially deleterious air is removed from the vessel thereby permitting more efficient transfer of gaseous HF. Liquid nitrogen facilitates transfer of HF by condensing gaseous HF. The autoclave is then attached to an HF cylinder and the desired amount of HF is vacuum transferred into the autoclave.

The quantities of chloroethene, HF, and tin catalyst present in the vessel may vary over a broad range of effective operation. The quantity of materials used in the process of the current invention is generally between about 0.1 to at least about 10 (lb chloroethene fed/hour)/lb catalyst, usually about 0.2 (lb chloroethene fed/hour)/lb catalyst when the tin catalyst comprises $SnCl_4$. The initial amount of catalyst charged with HF is generally between about 5 to at least about 35 weight %, for example, $SnCl_4$ in HF, normally from about 10 to about 20 weight % catalyst in HF.

After the starting materials are introduced into the sealed autoclave, the autoclave is then detached from the vacuum and HF sources, and allowed to warm to ambient temperature. The autoclave is then placed into a heating jacket designed for the autoclave, and heated to a temperature of about 30 to about 130° C., normally about 50° to about 95° C., and the total pressure within the autoclave is maintained between about 10 and about 400 psi, normally 50 psi. The pressure within the autoclave can be maintained by using any suitable means such as a back pressure regulator.

Gaseous chloroethene is then added to the autoclave at a rate that varies as a function of the amount of HF and tin catalyst within the autoclave, e.g., adding chloroethene at a rate of about 10 to about 100 sccm (about 0.01 to about 0.5 g/hr/g-catalyst). A gaseous effluent exiting a reflux condenser, which is in fluid communication with the autoclave, is collected by condensation and monitored. The composition of the effluent is monitored by using an on-line gas chromatograph (GC). After the addition of chloroethene has ceased, the autoclave is vented of excess gaseous and liquid materials by a nitrogen purge. The solid contents of the autoclave are then removed, drowned with water and filtered. The filtrate is rinsed with 10% aqueous hydrochloric acid, water, and dried in a vacuum oven to a constant mass. The composition of the dried mass is also analyzed in order to determine the amount of tar that was formed.

Figure 1:
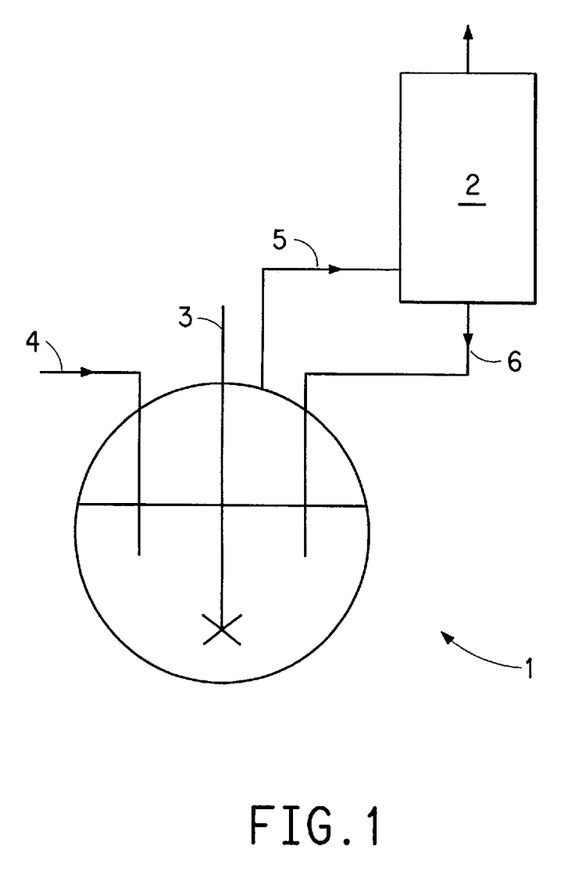

While the aforementioned batch process can be employed, a continuous process is particularly desirable from an industrial standpoint. Referring now to FIG. 1, FIG. 1 is a schematic diagram for a continuous HFC-152a manufacturing process. A reactor 1 is in fluid communication with a reflux column 2. Typically, the reflux column 2 will have a reflux ratio of between about 2 to about 20 when operated at a pressure of about 50 to about 400 psi and a temperature of about 50 to about 150 C. Predetermined amounts (as previously discussed for batch process) of HF and at least one catalyst are added to the reactor 1. The contents of the reactor 1 are agitated by using a dual bladed agitator with pump down action 3, heated, and brought to reflux at the desired operating temperature/pressure. When the desired operating conditions have been established, IF and chloroethene are fed continuously to the reactor via one or more feed lines 4. Gas exits from the reactor 1 and is transported to the reflux column 2 via one or more feed lines 5. The gas stream leaving the reflux column 2 typically consists essentially of HFC-152a and HCl, e.g., about 60 to about 70 wt % HFC-152a. A liquid return line 6 is connected to the bottom of the reflux column 2. Line 6 returns high boiling intermediates such as 1,1-dichloroethane, HCFC-151a, among others, and any HF to reactor 1. The gas stream leaving the reactor 1 or reflux column 2 can be purified by any suitable manner such as by using two conventional distillation steps (not shown in FIG. 1). The first distillation step removes HCl. The second distillation step removes any unreacted intermediates and HF that are recovered and, if desired, recycled to reactor 1.

Similar to operating a batch process, the production equipment and its associated feed lines, effluent lines and any handling units should be constructed of materials resistant to HF and HCl. Typical materials of construction, well-known to the fluorination art, include stainless steels and the high nickel alloys, such as Monel® nickel-copper alloys, Hastelloy® nickel-based alloys and, Inconel® nickel-chromium alloys.

While the previous description has placed particular emphasis upon making a product stream wherein HFC-152a as the major component, the inventive process can also be operated in a manner which produces other desirable compounds. That is, the inventive process can produce HFC-152a alone or co-produced with one or more of HCFC-141b (1,1-dichloro-1-fluoroethane), HCFC-142b (1-chloro-1,1-difluoroethane), HFC-143a (1,1-trifluoroethane), among others, e.g., from a hydrochlorocarbon such as 1,1-dichloroethene. The co-produced product can be recovered and employed as a useful mixture, or separated into its individual components.

The following examples are provided for the purpose of further illustrating the present invention without limiting the invention as defined in the appended claims. In the following Examples, chloroethene was supplied by FlukaIncorporated, Ronkonkoma, N.Y., ET was supplied by Air Products (Allentown, Pa.) and nonionized NaCl was supplied by Morton Salt, Chicago, Ill. All compounds employed in the following Examples were commercially available.

Example 1—KF Additive

Commercially available tin tetrachloride ($SnCl_4$, about 37.5 g, 0.144 mol) and potassium fluoride (KF, 1.25 g, 0.0215 mol) were added to a Hastelloy C® 450 cc Parr® Series 4560 Mini Reactor that was housed within a dry box. The reactor head, which was equipped with a 0.25 inch tube reflux condenser, was attached to the autoclave, removed from the drybox and connected to a stainless steel vacuum line. The base of the reactor was immersed in liquid nitrogen. HF (about 150 g, 7.5 mol) was vacuum transferred into the reactor. The liquid nitrogen cooling bath was removed, the temperature of the reactor was raised by using external heating until the internal temperature was about 25° C., and cooling water (3.7° C.) was circulated through the condenser. A heating jacket was placed around the reactor, and the internal temperature of the reactor was increased to about 50° C. while maintaining the internal pressure at about 50 psi by using a back pressure regulator.

The flow of chloroethene (about 44.1 standard cubic cm/minute or sccm, $7.4 \times 10^{-7}$ $m^3$/sec) and methane (9.8 sccm, $1.6 \times 10^{-7}$ $m^3$/sec) were begun. In all of the Examples, except 10 and comparative 3, methane was introduced into the reactor as a standard for the gas chromatograph as well as diluent to assist in removing material from the reactor.

A gaseous effluent from the reactor was monitored every hour for the approximately 16.7 hours of chloroethene addition. The molar yield of HFC-152a based on the chloroethene fed was measured to be about 97%. The HFC-152a was found by on-line GC to be about 100% of the effluent. The ratio of HFC-152a/HCFC-151a (averaged from the 4th to the 16th hour of the experiment) as measured by GC was about 48. At the end of the run, the reactor was vented to atmospheric pressure to drive off volatiles, e.g., HF and organics. Further removal of volatiles was assisted by using a nitrogen purge. Any solids remaining in the autoclave were drowned in water and filtered on a Teflon® membrane filter. The filtrate was washed with 10% HCl and then with water, and dried at a temperature of about 115° C. in a convection oven to constant mass. The tars formed over this run averaged about 1.00 g per 100 g chloroethene fed.

Comparative Example 1—No Alkali Metal Halide Additive

The apparatus, procedure, and materials used for this Comparative Example were substantially identical to those discussed for Example 1, with the exception that no alkali metal salt additive was used.

The molar yield of HFC-152a based on the chloroethene fed was measured to be about 85%. The HFC-152a product as measured by an on-line GC was found to be about 98% of the effluent. The ratio of HFC-152a/HCFC-151a (averaged from the 4th to the 17th hour of the experiment) was measured to be about 40. After approximately 18 hours of operation, the reactor was cooled and vented to atmospheric pressure to drive off volatiles, e.g., HF and organics. Further removal of volatiles was assisted by a nitrogen purge. Any solids remaining in the autoclave were drowned in water and filtered on a Teflon® membrane filter. The filtrate was washed with 10% HCl and then with water, and dried at a temperature of about 115° C. in a convection oven to constant mass. The tars formed over this run averaged about 2.30 g per 100 g chloroethene fed.

Table 2—Examples 1 through 9 and Comparative Examples 1 and 2

Examples 2–9 employed a procedure substantially identical to that disclosed in Example 1, and Comparative Example 2 employed a procedure substantially identical to Comparative Example 1. In the case of Examples 5, 6, 7, 8 and Comparative Example 2, aliquots of reactor mass of about 20–70 grams were taken immediately at the end of the run and were analyzed for the presence of elemental tin. The results of Examples 2–9 are listed below in Table 2. The process variables, which were altered from the Example 1, and the reaction products are also reported in Table 2. The process variables which remained constant throughout the runs are listed in the Notes immediately following Table 2.

TABLE 2

| Ex[a] | Alkali Metal Halide, Mole Ratio Alkali Metal Halide/ Tin Catalyst | Chloro- ethene Flow (sccm)[b] | Rxn. Time (hr) | Molar Yield[e] HFC-152a | Product Mole Ratio 1521a/151a | Grams Tar per 100 g Chloro- ethene Fed | % Tin in Reactor Mass |
|---|---|---|---|---|---|---|---|
| 1 | KF, 0.15 | 44.1 | 16 | Quantitative | 48 | 1.0 | — |
| 2 | KF, 0.30 | 42.0 | 17 | Quantitative | 58 | 0.67 | — |
| 3 | KF, 0.60 | 42.0 | 16.3 | Quantitative | 68 | 0.41 | — |

TABLE 2-continued

| Ex[a] | Alkali Metal Halide, Mole Ratio Alkali Metal Halide/ Tin Catalyst | Chloro- ethene Flow (sccm)[b] | Rxn. Time (hr) | Molar Yield[e] HFC-152a | Product Mole Ratio 1521a/151a | Grams Tar per 100 g Chloro- ethene Fed | % Tin in Reactor Mass |
|---|---|---|---|---|---|---|---|
| 4 | KF, 1.9 | 42.0 | 17 | 96 (93% pure) | 21 | 4.86 | — |
| 5 | KF, 1.0 | 50.2 | 15.5 | 88 (99% pure) | 78 | 0.15 | 13.4 |
| 6 | KCl, 1.0 | 50.2 | 15.5 | 87 (99% pure) | 96 | 0.14 | 14.4 |
| 7 | NaCl, 1.0 | 50.1 | 15.5 | 85 (99% pure) | 105 | 0.21 | 14.4 |
| 8c | NaF, 1.0 | 50.2 | 15.5 | 88 (99% pure) | 99 | 0.29 | 11.1 |
| 9 | NaCl, 0.50 | $CCl_3CH_3$ 12.2 Chloroeth ene 25.3 | 14 | 143a 68.4 142b 29.9 152a 98.3 | 143a/142b 2.3 152a/151a 49 | 0.70 g | — |
| C1 | None | 49.2 | 16.5 | 85 (98% pure) | 41 | 2.3 | — |
| C2 | None | 49.2 | 16.3 | 87 (98% pure) | 44 | 2.03 | 5.4 |
| 10 | KF, 0.60 | d | d | d | 59 | 3.5 | — |
| C3 | None | d | d | d | 11 | 7.12 | — |

Notes Pertaining to Table 2
[a]: All examples (except for 4, 10 and C3) used 0.144 mole $SnCl_4$. Example 4 used 0.0768 mole $SnCl_4$. All examples (except for 10 and C3) used 7.5 mole of anhydrous HF. All examples were carried out at 50° C. and 50 psi for the time specified in the "Rxn. Time (hrs)" column.
[b]: sccm = standard cubic centimeters/minute
[c]: See experimental description which follows. Amounts of materials were the same but the addition order changed.
[d]: See experimental description which follows for example 10 and comparative example 3. The procedure was slightly different than Examples 1–9 and comparative examples 1 and 2.
[e]: Moles of 152a are calculated by reference to the internal flow of methane.

Examples 5–8, and Comparative Example 2 were carried out as described above with the exception that at the end of the run, an evacuated cylinder was attached to a reactor dip tube and a portion of the reactor mass was removed for analysis of elemental tin. The results of these Examples were also reported above in Table 2.

Example 5—KF Additive

The apparatus, procedure, and materials used for this Example were substantially identical to those described above in Example 1. Potassium fluoride (KF, about 8.37 gm, 0.144 mol) was charged to the reactor along with tin tetrachloride. Chloroethene was added at a rate of about 50.2 sccm ($8.37 \times 10^{-7}$ m³/sec) with internal standard methane being added at rate of about 9.8 sccm ($1.63 \times 10^{-7}$ m³/sec). The gaseous effluent was monitored every hour during an approximately 15.5 hours of chloroethene addition. The molar yield of HFC-152a based on the chloroethene fed was about 88% by GC comparison to methane. The HFC-152a was analyzed by an on-line GC to be about 99% by GC analysis of the effluent. The ratio of HFC-152a/HFC-151a (averaged from the 4th to the 15th hour of the experiment) as measured by GC was about 78. At the end of the run and immediately after the agitator had stopped, an approximately 39.3 g sample of the reactor mass was removed through the dip tube of the reactor by temporarily connecting an evacuated cylinder to the lines which normally used for feeding chloroethene and methane. The sample was analyzed by using X-ray fluorescence to contain about 13.4% by wt Sn. The reactor was vented to atmospheric pressure to remove any volatiles, e.g., HF and organics. Further removal of organics was assisted by a nitrogen gas purge. The solids remaining in the autoclave were drowned in water and filtered on a Teflon® membrane filter. The filtrate was washed with 10% HCl and then with water, and dried in a convection oven at a temperature of about 115° C. to a constant mass. The tars formed over this run averaged about 0.15 g per 100 g chloroethene fed.

Example 8—Late Charge of NaF Additive

Tin tetrachloride ($SnCl_4$, about 37.5 gm, 0.144 mol) was added to a Hastelloy C® 450 cc Parr® Series 4560 Mini Reactor that was housed within a dry box. A reactor head, which was equipped with a 0.25 inch tube reflux condenser, was attached to the Mini Reactor. The reactor was removed from the drybox and connected to a stainless steel vacuum line. The base of the reactor was immersed within liquid nitrogen, and HF (100 g, about 5.0 mol) was vacuum transferred into the reactor. The liquid nitrogen cooling bath was removed, the temperature of the reactor raised by using external heating until the internal temperature was about 25° C., and cooling water (about 3.7° C.) began circulating through a condenser located attached to the reactor head. A heating jacket was placed around the reactor, and the internal temperature of the reactor was increased to about 50° C. while maintaining the internal pressure at about 50 psi by using a back pressure regulator. The contents of the reactor were contacted and permitted to react for about two hours under the previously described conditions thereby allowing the $SnCl_4$ catalyst and HF to form a tin chlorofluoride catalyst. After this two hour period, a pressurized solution of NaF (6.00 g, about 0.143 mol) in HF (50 g, about 2.5 mol) was injected into the catalyst solution. The resultant mixture was stirred for about 15 minutes, at which time the flow of chloroethene (about 50.2 sccm, $8.37 \times 10^{-7}$ m³/sec) and an internal standard methane (about 9.4 sccm, $1.57 \times 10^{-7}$ m³/sec) were begun The gaseous effluent, which was exiting the reactor, was analyzed every hour for the 15.5 hours of chloroethene addition. The molar yield of HFC-152a based on the chloroethene fed was determined by GC to be about 88% by comparison to the methane standard. The HFC-152a was measured by on-line GC to be about 99% of the effluent. The ratio of HFC-152a/HCFC-151a (averaged from the 4th to the 15th hour of the experiment) as measured by GC was about 99. At the end of the run, an approximately 20.4 g sample of the reactor mass was taken through a dip tube immediately after the agitator had stopped. The sample was analyzed by X-ray fluorescence to contain about 11.1% by wt Sn, as elemental tin. The reactor was vented to atmospheric pressure to remove volatiles, e.g., HF and organics. Further removal of organics was assisted by a nitrogen purge. The solids remaining in the autoclave were drowned in water and filtered on a Teflon® membrane filter. The filtrate was washed with 10% HCl and then with water, and dried in a convection oven at a temperature of about 115° C. to constant mass. By using gravimetric analysis, it was determined that the tars formed over this run averaged about 0.29 g per 100 g chloroethene fed.

Comparative Example 2

No Alkali Metal Halide Additive

The apparatus, procedure, and materials used for this Example were substantially identical to those discussed for Comparative Example 1.

The flow of chloroethene to the reactor was approximately 49.2 sccm (8.2×10⁻⁷ m³/sec) and an internal standard methane was about 9.8 sccm (1.6×10⁻⁷ m³/sec). A gaseous effluent exiting the reactor was monitored every hour during approximately 16.3 hours of chloroethene addition. The molar yield of HFC-152a as based on the chloroethene fed was 87%. The HFC-152a was found by on-line GC to be 98% of the effluent. The ratio of HFC-152a/HCFC-151a (averaged from the 4th to the 16th hour of the experiment), which was measured by using an GC, was 44. At the end of the experiment, an approximately 21.6 g sample of the reactor mass was removed from the reactor via a dip tube immediately after the agitator had stopped. The sample was found to contain about 5.4% Sn that was measured as elemental tin by using X-ray fluorescence. The reactor was vented to atmospheric pressure to remove volatiles, e.g., HF and organics. Further removal of organics was assisted by using a nitrogen purge. The solids remaining in the autoclave were drowned in water and filtered on a Teflon® membrane filter. The filtrate was washed with 10% HCl and then with water, and dried in a convection oven at a temperature of about 115° C. to constant mass that corresponded to tars. The tars formed over this experiment averaged about 2.03 g per 100 g chloroethene fed.

Example 9—NaCl Additive

The apparatus, procedure, and materials used for this Example were substantially identical to those discussed in Example 1.

Sodium chloride (NaCl, about 4.21 g or 0.072 mol) was charged to the reactor along with the tin tetrachloride. HCC-140a or 1,1,1-Trichloroethane was added to the reactor at a rate of about 12.2 sccm (2.03×10⁻⁷ m³/sec), chloroethene at a rate of about 25.3 sccm (4.23×10⁻⁷ m³/sec); and an internal standard methane at a rate of about 10.3 sccm (1.7×10⁻⁷ m³/sec). The gaseous effluent exiting the reactor was monitored every hour during the 14 hours of continuous material addition. The gaseous effluent comprised molar yields of 1,1,1-trifluoroethane (HFC-143a, based on 1,1,1-trichloroethane), 1-chloro-1,1-difluoroethane (HCFC-142b, based on 1,1,1-trichloroethane), and HFC-152a (based on chloroethene) were determined to be about 68.4%, 29.9%, and 98.3%, respectively. The mole ratio of HFC-143a/HCFC-142b (averaged from the 5th to the 14th hour of the experiment) was determined to be about 2.3, and the ratio of HFC-152a/HCFC-151a was determined to be about 49. At the end of the experiment, the reactor was vented to atmospheric pressure to remove volatiles, e.g., HF and organics. Further removal of organics was assisted by using a nitrogen gas purge. The solids remaining in the autoclave were drowned in water and filtered on a Teflon® membrane filter. The filtrate was washed with 10% HCl and then with water, and dried in a convection oven at a temperature of about 115° C. to constant tars mass. The tars formed over this run averaged about 0.70 g per 100 g chloroethene fed.

Example 10—KF Additive

Tin tetrachloride (SnCl$_4$ about 100 g or 0.383 mol) and potassium fluoride (KF about 13.4 g or 0.230 mol) were added to a Hastelloy C® 600 cc Parr® Mini Reactor that was housed in a dry box. The reactor head was equipped with two ports for feed or sampling, a reflux column with a port for collecting exiting vapors, and an agitator. The reactor was sealed to the base, the base cooled, and HF (about 300 g or 15 mol) was transferred into the reactor. The resulting mixture was allowed to digest for approximately 15 hours. The contents of the reactor were then heated to a temperature of about 80° C., and agitation and chloroethene feed began. HF was then introduced into the reactor and the feed rate adjusted so as to maintain a constant weight of material in the reactor. After the HF introduction achieved a constant weight in the reactor and successive on-line GC analyses of the reflux condenser effluent were within experimental error, the process was consider to be at "steady state". At an approximately 19.6 g/hr chloroethene feed rate, the following steady state results were measured by using an on-line GC analysis of the reflux condenser effluent: HFC-152a (about 97.9% by GC peak area integration), chloroethene (about 0.017%), HCFC-151a (about 1.7%) and 1,1-dichloroethane (about 0.2%). The relative molar ratio of HFC-152a/HCFC-151a was found by GC to be about 59. At the end of this experiment, tar solids were obtained substantially in the manner described in Example 1. The tars formed over this experiment averaged about 3.5 g per 100 g of chloroethene fed.

Comparative Example 3—No Alkali Metal Halide Additive

The apparatus, procedure, and materials used for this Comparative Example were substantially identical to those described in Example 10.

The initial materials charged into the reactor were tin tetrachloride (about 140 g or 0.56 mol) and HF (about 300 g or 15 mol). A steady-state reaction was carried out at a temperature of about 76° C. At an approximately 18.2 g/hr chloroethene feed rate, the following steady state conditions were measured by an on-line GC analysis of the reflux condenser effluent: HFC-152a (about 89.6% by GC peak integration), chloroethene (about 0%), HCFC-151a (about 7.8%), and 1,1-dichloroethane (about 2.4%). The relative ratio of HFC-152a/HCFC-151a was determined by using GC to be about 11. At the end of the experiment, tar solids were obtained substantially in the manner described in Example 1. The tars formed over this run averaged about 7.12 g per 100 g of chloroethene fed.

The following Examples 11 and 12 illustrate that even when employing relatively low catalyst concentrations, the presence of an additive is desirable.

Example 11

SnCl$_4$ (2.61 gm, 0.01 mol) was added to a Hastelloy® C 450 cc Parr® Series 4560 Mini Reactor in a dry box. The reactor head, which was equipped with a small ¼" tube reflux condenser, was attached and removed from the drybox; it was connected to a stainless steel vacuum line. The bottom of the reactor was immersed into liquid nitrogen and HF (150 gm, 7.5 mol) was transferred in from a 4 lb cylinder. The liquid nitrogen was removed, and the temperature of the reactor was raised using external heating (hot air gun) until the internal temperature was about 25° C., and cooling water (3.7° C.) was turned on to the condenser. A fabric heating jacket was put around the reactor, and the internal temperature of the reactor was raised to 50° C. and 50 PSI (controlled by a back pressure regulator), at which time the flow of chloroethene (about 50.1 sccm, 8.4×10$^{-7}$ m$^3$/sec) and methane (about 9.4 sccm, 1.6×10$^{-7}$ m$^3$/sec) used as an internal standard were begun The gaseous effluent was monitored every hour for the 16.5 hours of chloroethene addition. The absolute yield of 1,1-difluoroethane based on the chloroethene fed was about 78%. The 1,1-difluoroethane measured by on-line gas chromatography to be approximately 96% of the effluent. The ratio of 152a/151a (averaged from the 4th to the 16th hour of the experiment) was also measured by GC to be about 29. At the end of the run, the reactor was vented to atmospheric pressure to drive off volatiles (HF and organics). The volatiles were removed under a nitrogen purge. The solids remaining in the autoclave were drowned in water and filtered on a Teflon membrane filter. The filtrate was washed with 10% HCl and then with water and dried in a vacuum oven. The tar formation rate was about 3.03 g tars per 100 g chloroethene fed.

Example 12

Using procedures described in the previous examples, SnCl$_4$ (50.0 gm, 0.192 mol), NaCl (9.02 gm, 0.155 mol), and HF (150 gm, 7.5 mol) were reacted overnight at a temperature of about 50° C. and a pressure of about 50 psi. The pressure of the autoclave was reduced and the pressure dropped to ambient and the volatiles were removed and scrubbed. The contents of the reactor were then pumped on at ambient temperature using a vacuum pump through an HF scrubber which employed NaF pellets. The autoclave was taken into the drybox and approximately 35.6 gm of a white solid was isolated.

The white solid (3.1 gm, 0.011 mole Na$_{0.8}$SnCl$_{2.8}$F$_2$) was added to a Hastelloy® C 450 cc Parr® Series 4560 Mini Reactor in a dry box. The reactor head, which was equipped with a small ¼" tube reflux condenser, was attached and removed from the drybox; it was connected to a stainless steel vacuum line. The bottom of the reactor was immersed in liquid nitrogen and HF (150 gm, 7.5 mol) was transferred in from a 4 lb cylinder. The liquid nitrogen was removed, and the temperature of the reactor was raised using external heating (hot air gun) until the internal temperature was about 25° C., and cooling water (3.7° C.) was turned on to the condenser. A fabric heating jacket was put around the reactor, and the internal temperature of the reactor was raised to about 50° C. and about 50 psi (controlled by a back pressure regulator), at which time the flow of chloroethene (about 50.2 sccm, 8.4×10$^{-7}$ m$^3$/sec) and methane (about 9.4 sccm, 1.6×10$^{-7}$ m$^3$/sec) used as an internal standard were begun The gaseous effluent was monitored every hour for the 16.5 hours of chloroethene addition. The absolute yield of 1,1-difluoroethane based on the chloroethene fed was approximately 72%. The 1,1-difluoroethane measured by on-line gas chromatography to be approximately 96% of the effluent. The ratio of 152a/151a (averaged from the 4th to the 16th hour of the experiment) was also measured by GC to be about 29. At the end of the run, the reactor was vented to atmospheric pressure to drive off volatiles (HF and organics). The volatiles were removed under a nitrogen purge. The solids remaining in the autoclave were drowned in water and filtered on a Teflon membrane filter. The filtrate was washed with 10% HCl and then with water and dried in a vacuum oven. The tar formation rate was about 2.48 g tars per 100 g chloroethene fed.

The following is claimed:

1. A process for making 1,1-difluoroethane comprising:
    preparing a first mixture comprising chloroethene and hydrogen fluoride,
    adding a tin-containing catalyst and an alkali metal halide to the first mixture, and;
    recovering a product comprising 1,1-difluoroethane.

2. A process for reducing tar formation in 1,1-difluoroethane manufacture comprising:
    contacting chloroethene, hydrogen fluoride and a tin-containing catalyst in a vessel while in the presence of an alkali metal halide,
    heating the vessel,
    recovering an effluent comprising 1,1-difluoroethane from the vessel wherein the recovered effluent is substantially free of oligomeric and polymeric compounds.

3. The process of claim 1 or 2 wherein the catalyst comprises at least one member from the group consisting of SnCl$_4$, SnBr$_4$, SnCl$_3$F, SnCl$_2$F$_2$, SnClF$_3$, SnF$_4$, SnCl$_2$O, SnF$_2$O, SnClFO, Sn(CH$_3$)$_4$, OSn(C$_2$H$_5$)$_2$ and SnCl$_2$(CH$_3$)$_2$.

4. The process of claim 1 or 2 wherein the ratio of alkali metal halide to catalyst is greater than about 0 to about 2.0.

5. The process of claim 1 or 2 wherein the molar yield of 1,1-difluoroethane is greater than about 85% and the molar ratio of 1,1-difluoroethane 1,1-chlorofluoroethane is greater than 45.

6. The process of claim 1 or 2 wherein the alkali metal halide comprises at least one member from the group consisting of KF, KCl, NaCl and NaF.

7. The process of claim 1 or 2 wherein the process is performed in a liquid phase.

8. The process of claim 1 or 2 wherein the process is practiced at a temperature of about 20° to 130° C.

9. The process of claim 1 or 2 wherein said 1,1-difluoroethane further comprises at least one of HFC-143a and HCFC-142b.

10. The process of claim 1 or 2 wherein said process is continuous process.

11. The process of claim 1 or 2 wherein said catalyst and alkali metal halide are premixed prior to said contacting.

12. The process of claim 1 or 2 wherein the catalyst comprises SnCl$_4$ and the alkali metal halide comprises NaCl.

13. A process for making 1,1-difluoroethane comprising the steps of:

providing a reaction vessel containing a liquid phase comprising a tin containing catalyst, HF and at least one alkali metal halide, contacting the liquid phase with chloroethene, heating the liquid phase to a temperature from about 20° to 130° C., distilling the liquid phase, and;

recovering substantially pure 1,1-difluoroethane.

14. The process of claims 1, 2 or 3 wherein said chloroethene further comprises 1,1-dichloroethane.

15. The process of claims 1, 2 or 3 wherein said catalyst consists essentially of a tin chlorofluoride formed by contacting tin chloride with HF and said alkali metal halide consists essentially of NaCl.

16. The process of claims 1, 2 or 3 wherein said process is operated while in the presence of at least one member selected from the group consisting of methylene chloride, 1,2-dichloroethane, 1,1-dichloroethane, 1-chloro-1-fluoroethane, and 2,2-dichloro-1,1,1- trifluoroethane.

17. The process of claim 16 wherein said member comprises 2,2-dichloro-1,1,1-trifluoroethane.

* * * * *

UNITED STATES PATENT AND TRADEMARK OFFICE
CERTIFICATE OF CORRECTION

PATENT NO.    : 5,866,728
DATED         : February 2, 1999
INVENTOR(S)   : Nappa et al.

It is certified that error appears in the above-identified patent and that said Letters Patent is hereby corrected as shown below:

Column 15,
Line 10, delete "1".
Line 10, delete "or"; place a comma (,) after "2"; insert -- or 13 -- so dependency reads "2, 3 or 13".
Line 12, delete "1".
Line 12, delete "or"; place a comma (,) after "2"; insert -- or 13 -- so dependency reads "2, 3 or 13".

Column 16,
Line 3; delete "1".
Line 3, delete "or"; place a comma after "2"; insert -- or 13 -- so dependency reads "2, 3 or 13".

Signed and Sealed this

Twenty-sixth Day of February, 2002

Attest:

Attesting Officer

JAMES E. ROGAN
Director of the United States Patent and Trademark Office